(12) United States Patent
Levin

(10) Patent No.: US 11,406,541 B2
(45) Date of Patent: Aug. 9, 2022

(54) MULTI-LAYER TUBULAR ELASTICIZED WOUND DRESSING

(71) Applicant: The Trustees of Columbia University in the City of New York, New York, NY (US)

(72) Inventor: Laura E. Levin, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 478 days.

(21) Appl. No.: 16/461,497

(22) PCT Filed: Nov. 27, 2017

(86) PCT No.: PCT/US2017/063244
§ 371 (c)(1),
(2) Date: May 16, 2019

(87) PCT Pub. No.: WO2018/098418
PCT Pub. Date: May 31, 2018

(65) Prior Publication Data
US 2019/0314208 A1    Oct. 17, 2019

Related U.S. Application Data

(60) Provisional application No. 62/426,791, filed on Nov. 28, 2016.

(51) Int. Cl.
*A61F 13/00* (2006.01)
(52) U.S. Cl.
CPC .. *A61F 13/00038* (2013.01); *A61F 13/00029* (2013.01); *A61F 13/00987* (2013.01);
(Continued)

(58) Field of Classification Search
CPC ............................................. A61F 2013/00217
See application file for complete search history.

(56) References Cited

U.S. PATENT DOCUMENTS

| 4,176,664 A | * | 12/1979 | Kalish ................. A61F 13/0203 602/57 |
| 4,506,611 A | | 3/1985 | Parker et al. |
| (Continued) | | | |

FOREIGN PATENT DOCUMENTS

| CN | 104024498 A | 9/2014 |
| CN | 105007871 A | 10/2015 |
| (Continued) | | |

OTHER PUBLICATIONS

Arthor Unkown, "Mepilex Dressings Datacard", May 21, 2009, Retrieved from the internet: URL: http://www.dressings.org/Dressings/mepilex.html.
(Continued)

*Primary Examiner* — Kim M Lewis
(74) *Attorney, Agent, or Firm* — Baker Botts, L.L.P.

(57) ABSTRACT

A wound dressing is made from a tubular inner layer and at least one outer layer disposed radially beyond the inner layer. The inner layer permits egress of fluid from weeping wounds, prevents desiccation of skin disposed beneath the inner layer, and prevents desiccation of ointment disposed between the inner layer and the skin. The at least one outer layer absorbs fluids that leak through the inner layer, protects the inner layer from outside contaminants, and prevents fluids from escaping. The at least one outer layer is affixed to the inner layer, and each of the layers is elastic in at least the radial direction. Optionally, a layer of ointment may be applied to an inner surface of the inner layer. Note that the tubular inner layer may be either pre-formed or formed at the time of application.

19 Claims, 2 Drawing Sheets

(52) U.S. Cl.
CPC ........... *A61F 2013/00093* (2013.01); *A61F 2013/00131* (2013.01); *A61F 2013/00217* (2013.01); *A61F 2013/00285* (2013.01)

(56) References Cited

U.S. PATENT DOCUMENTS

| | | | |
|---|---|---|---|
| 4,889,063 | A | 12/1989 | Bompard et al. |
| 4,926,851 | A * | 5/1990 | Bulley .................. A61F 13/105 128/856 |
| 5,437,621 | A * | 8/1995 | Andrews ................. A61L 15/26 2/21 |
| 5,474,525 | A * | 12/1995 | Blott ..................... A61F 13/041 602/63 |
| 6,580,011 | B1 * | 6/2003 | Jennings-Spring ........................ A61F 13/00021 602/41 |
| 8,777,886 | B2 | 7/2014 | Mueller |
| 8,834,395 | B2 | 9/2014 | Becker et al. |
| 2002/0095107 | A1 * | 7/2002 | Martin .................. A61F 13/105 602/61 |
| 2006/0094997 | A1 | 5/2006 | Kurata |
| 2008/0027365 | A1 * | 1/2008 | Huey ..................... A61L 15/44 602/44 |
| 2008/0033329 | A1 * | 2/2008 | Downs ................. D06M 13/432 602/41 |
| 2010/0100025 | A1 * | 4/2010 | Kane .................. A61B 17/1322 602/79 |
| 2010/0168634 | A1 | 7/2010 | Leeming et al. |
| 2013/0102944 | A1 * | 4/2013 | DiGrazia ............ A61F 13/0273 602/43 |
| 2014/0135676 | A1 * | 5/2014 | De Man ............ A61F 13/00029 602/43 |
| 2014/0309574 | A1 | 10/2014 | Cotton |
| 2015/0157524 | A1 * | 6/2015 | Reid, Jr. ................. A61H 1/008 601/84 |
| 2019/0117231 | A1 * | 4/2019 | McEwen ................. A61F 13/10 |
| 2019/0262188 | A1 * | 8/2019 | Reid, Jr. ............. A61B 5/6804 |

FOREIGN PATENT DOCUMENTS

| | | | |
|---|---|---|---|
| EP | 0617938 A1 | 10/1994 | |
| EP | 0528091 B1 | 4/1997 | |
| GB | 1004064 A * | 9/1965 | ............ A61L 15/50 |
| GB | 1004064 A | 9/1965 | |
| GB | 2409977 A | 7/2005 | |
| WO | 8403832 A1 | 10/1984 | |
| WO | 0134079 A1 | 5/2001 | |
| WO | WO 2005/000372 A1 | 1/2005 | |
| WO | 2016067015 A1 | 5/2016 | |

OTHER PUBLICATIONS

Bishoff et al., "Dressing for Surgical Wounds of the Penis", Urology, vol. 47, Issue 2, Feb. 1996.
Gardon-Mollard, "Tubular Compression in the Treatment of Venous Ulcers of the Leg: A New Graduated Tubular Device", Phlebology, vol. 15, Issue 3, pp. 169-174, Nov. 2000.
International Preliminary Report on Patentability and Written Opinion dated May 28, 2019 and issued in International Application No. PCT/US2017/063244.
Kadir Bilisik, "Multiaxis Three Deminsional (3D) Woven Fabric", Erciyes University Department of Textile Engineering, Advances in Modern Woven Fabrics Technology, pp. 79-106, Jul. 27, 2011.
Vargas et al., "Hyperbranched polyglycerol electrospun nanofibers for wound dressing applications" Acta Biomaterialia, vol. 6, Issue 4, Mar. 2010.
Wang et al., "The tubular elastic net bandage: a useful penile dressing in pediatric hypospadias", Indian Journal of Surgery, vol. 77, pp. 1425-1427, Dec. 2015.
Weller et al., "Randomized clinical trial of three-layer tubular bandaging system for venous leg ulcers" Wound Repair and Regeneration, vol. 20, Issue 6, pp. 8220829, Nov. 2012.
Photo of Molnlycke tubipad limb bandage model 4581 (date unkown).

* cited by examiner

MULTI-LAYER TUBULAR ELASTICIZED WOUND DRESSING

CROSS REFERENCE TO RELATED APPLICATIONS

This Application is a US national stage filing under 35 U.S.C. § 371 of International Application No. PCT/US2017/063244, filed Nov. 27, 2017, which claims the benefit of U.S. Provisional Application 62/426,791 filed Nov. 28, 2016, each of which is incorporated herein by reference in its entirety.

BACKGROUND

Existing solutions for applying a dressing to limbs, digits, or other body parts when a patient has a fragile skin (e.g., epidermolysis bullosa "EB," elderly fragile skin), an impaired skin barrier (e.g., ichthyosis), inflammatory skin conditions (e.g. atopic dermatitis, allergic contact dermatitis to adhesive), traumatic injuries or burns, surgical sites, and conditions that involve sloughing of skin and exposed erosions are problematic. More specifically, the conventional technique for dressing these skin conditions typically involves applying an ointment to strips or panels of gauze or an alternative substrate, followed by placing or wrapping an additional absorbent layer around the affected limb, and subsequently covering everything with one or more outer layers. But this technique is often painful for the patient, time-consuming (e.g., an average of 1.5 hours twice a day for EB patients), messy, labor-intensive, and requires a relatively high level of skill that may not be available at the point of care.

The conventional wound dressing techniques can also put patients at risk for further skin trauma or damage (e.g., due to desiccation of the primary dressing and/or displacement of the layers from their intended position with resultant caustic rubbing against the skin) and subject them to repeated emotional trauma. In addition, conventional wound dressings frequently shift from their intended position, are often itchy, hot, or otherwise uncomfortable, and can limit mobility and hinder wearing clothing.

SUMMARY OF THE INVENTION

A variety of embodiments of multi-layer tubular wound dressings in which each layer is optimized to perform certain functions are described herein. The various layers within the tubular wound dressing work in cooperation with each other to form a wound dressing that is superior to conventional wound dressings in many ways.

One aspect of the invention is directed to a first wound dressing that comprises a tubular inner layer; a tubular first outer layer disposed adjacent to the inner layer and radially beyond the inner layer; and a tubular second outer layer disposed radially beyond the first outer layer. The tubular inner layer permits egress of fluid from weeping wounds, prevents desiccation of skin disposed beneath the inner layer, and prevents desiccation of ointment disposed between the inner layer and the skin. The first outer layer absorbs fluids that leak through the inner layer. The second outer layer protects the first outer layer and the inner layer from outside contaminants and prevents fluids from escaping. The first outer layer is affixed to the inner layer and the second outer layer is affixed to the first outer layer. Each of the inner layer, first outer layer, and second outer layer is elastic in a radial direction.

Some embodiments of the first wound dressing further comprise a layer of ointment that is applied to an inner surface of the inner layer.

In some embodiments of the first wound dressing, each of the inner layer, first outer layer, and second outer layer is sufficiently elastic in a radial direction to permit a diameter of the wound dressing to stretch to at least 150% of its diameter in an unstretched state. In some of these embodiments, each of the inner layer, first outer layer, and second outer layer is sufficiently elastic in an axial direction to permit a length of the wound dressing to stretch to at least 110% of its length in the unstretched state.

In some embodiments of the first wound dressing, the inner layer has properties that prevent or reduce adherence to wounds.

In some embodiments of the first wound dressing, the inner layer is formed from a plurality of threads or fibers, each of which is coated with a substance that prevents or minimizes adherence to the skin. In some of these embodiments, the substance comprises silicone.

In some embodiments of the first wound dressing, the first outer layer comprises fabric gauze. In some embodiments of the first wound dressing, the first outer layer is adjacent to the second outer layer. Some embodiments of the first wound dressing further comprise a layer of a foam material disposed between the first outer layer and the second outer layer.

In some embodiments of the first wound dressing, the first outer layer is affixed to the inner layer via stitching and the second outer layer is affixed to the first outer layer via stitching. In some of these embodiments, the stitching is applied as a plurality of zigzag strips that run in an axial direction.

In some embodiments of the first wound dressing, the first outer layer is affixed to the inner layer via stitching and the second outer layer is affixed to the first outer layer via stitching. These embodiments further comprise a layer of ointment that is applied to an inner surface of the inner layer. In these embodiments, each of the inner layer, first outer layer, and second outer layer is sufficiently elastic in a radial direction to permit a diameter of the wound dressing to stretch to at least 150% of its diameter in an unstretched state. In these embodiments, each of the inner layer, first outer layer, and second outer layer is sufficiently elastic in an axial direction to permit a length of the wound dressing to stretch to at least 110% of its length in the unstretched state. In these embodiments, the inner layer is formed from a plurality of threads or fibers, each of which is coated with a substance that prevents or minimizes adherence.

In some embodiments of the first wound dressing, at least one of the inner layer, the first outer layer, and the second outer layer is fabricated using at least one of circular weaving, circular knitting, 3D weaving, and 3D knitting. In some embodiments of the first wound dressing, the inner layer, the first outer layer, and the second outer layer are all fabricated together using at least one of 3D weaving and 3D knitting. In some embodiments of the first wound dressing, at least one of the inner layer, the first outer layer, and the second outer layer has a region of weakness that runs in an axial direction.

Another aspect of the invention is directed to a second wound dressing that comprises a tubular inner layer and at least one outer layer disposed radially beyond the inner layer. The tubular inner layer permits egress of fluid from weeping wounds, prevents desiccation of skin disposed beneath the inner layer, and prevents desiccation of ointment disposed between the inner layer and the skin. The at least one outer layer absorbs fluid that leaks through the inner layer, protects the inner layer from outside contaminants, and prevents fluids from escaping. The at least one outer layer is affixed to the inner layer, and each of the inner layer and the at least one outer layer is elastic in a radial direction.

Some embodiments of the second wound dressing further comprise a layer of ointment that is applied to an inner surface of the inner layer.

In some embodiments of the second wound dressing, each of the inner layer and the at least one outer layer is sufficiently elastic in a radial direction to permit a diameter of the wound dressing to stretch to at least 150% of its diameter in an unstretched state. In some of these embodiments, each of the inner layer and the at least one outer layer is sufficiently elastic in an axial direction to permit a length of the wound dressing to stretch to at least 110% of its length in the unstretched state.

In some embodiments of the second wound dressing, the inner layer has properties that prevent or reduce adherence to wounds.

In some embodiments of the second wound dressing, the inner layer is formed from a plurality of threads or fibers, each of which is coated with a substance that prevents or minimizes adherence. In some of these embodiments, the substance comprises silicone.

In some embodiments of the second wound dressing, the at least one outer layer comprises fabric gauze. In some embodiments of the second wound dressing, the at least one outer layer comprises an absorbent foam material.

In some embodiments of the second wound dressing, the at least one outer layer is affixed to the inner layer via stitching. In some of these embodiments, the stitching is applied as a plurality of zigzag strips that run in an axial direction.

In some embodiments of the second wound dressing, the at least one outer layer is affixed to the inner layer via stitching. These embodiments further comprise a layer of ointment that is applied to an inner surface of the inner layer. In these embodiments, each of the inner layer and the at least one outer layer is sufficiently elastic in a radial direction to permit a diameter of the wound dressing to stretch to at least 150% of its diameter in an unstretched state. In these embodiments, each of the inner layer and the at least one outer layer is sufficiently elastic in an axial direction to permit a length of the wound dressing to stretch to at least 110% of its length in the unstretched state. In these embodiments, the inner layer is formed from a plurality of threads or fibers, each of which is coated with a substance that prevents or minimizes adherence.

In some embodiments of the second wound dressing, at least one of the inner layer and the at least one outer layer is fabricated using at least one of circular knitting, circular weaving, 3D weaving, and 3D knitting. In some embodiments of the second wound dressing, the inner layer and the at least one outer layer are fabricated together using at least one of 3D weaving and 3D knitting. In some embodiments of the second wound dressing, at least one of the inner layer and the at least one outer layer has a region of weakness that runs in an axial direction.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
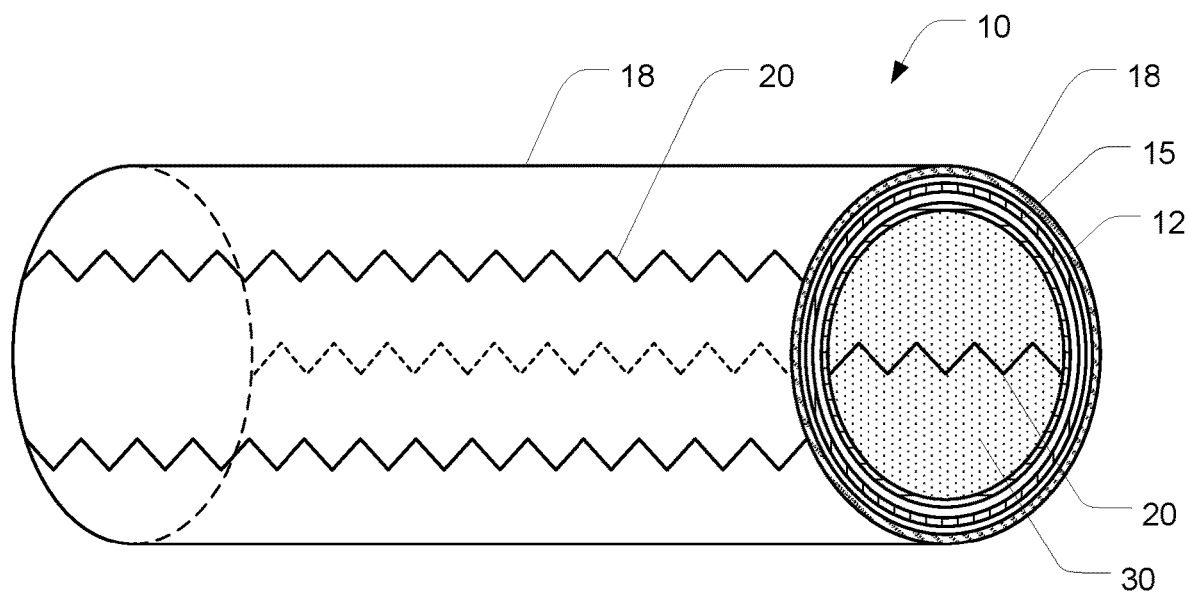
FIG. 1 depicts a multi-layer tubular elasticized wound dressing in a non-everted state.
Figure 2:
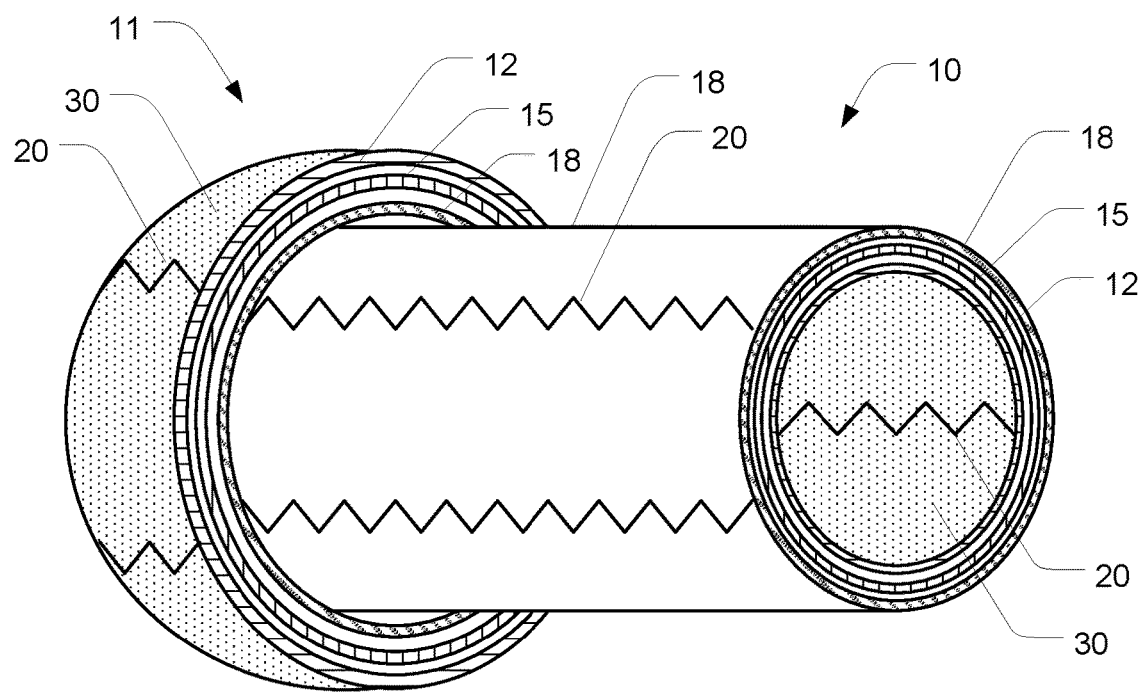
FIG. 2 depicts the FIG. 1 embodiment when a portion at one end of the wound dressing has been everted.

Many of the problems with the prior art approaches for applying wound dressings are overcome by the multi-layer elasticized wound dressings described herein. FIG. 1 depicts a first preferred embodiment of a multi-layer tubular elasticized wound dressing 10 in a non-everted state, and FIG. 2 depicts the same embodiment when a portion 11 at one end of the wound dressing 10 has been everted.

The wound dressing 10 depicted in FIG. 1 includes three layers: an inner layer 12 which sits closest to the patient's skin, a first outer layer 15 which surrounds the inner layer 12, and a second outer layer 18 which surrounds the first outer layer 15. Note that the terms inner and outer, as used herein, refer to the positions of the various layers with respect to a patient's limb after the wound dressing 10 has been applied to the limb. But the spatial relationship between those layers will be reversed whenever the wound dressing 10 is everted. (Thus, if the wound dressing 10 is everted, as seen on the left side of FIG. 2, the first outer layer 15 will be disposed radially beyond the second outer layer 18 and the inner layer 12 will be disposed radially beyond the first outer layer 15.)

In the FIG. 1 embodiment, each of the three layers 12, 15, 18 has different characteristics that, taken together, optimized the overall performance of the wound dressing 10 for dressing skin afflicted with a variety of conditions, including but not limited to the conditions mentioned above.

In many (but not all) situations, a layer of ointment 30 will be applied to the inner surface of the inner layer 12 before the wound dressing 10 is applied to the patient's limb. This layer of ointment 30 may be applied to the inner surface of the inner layer 12 by a practitioner or by the patient immediately prior to donning the wound dressing 10. Alternatively, the layer of ointment 30 may be pre-applied by the manufacturer. As yet another alternative, a layer of ointment may be applied to the surface of the limb before the wound dressing 10 is applied to the limb. In that situation, the layer of ointment 30 would not be applied (or pre-applied) to the inner surface of the inner layer 12 before the wound dressing 10 is applied to the patient's limb.

Examples of ointments 30 that may be applied to the inner surface of the inner layer 12 include but are not limited to 100% petrolatum, Aquaphor®, bacitracin and mupirocin. Depending on the condition being treated, the ointment 30 can provide one or more of the following benefits (1) promoting a moist environment thereby improving the skin barrier; (2) preventing the wound from drying and aiding in wound healing or skin barrier functions; (3) decreasing shearing forces on the skin by providing a slippery film thereby preventing injury to the skin; (4) serving as a seal to prevent outside contamination and infection; and (5) helping to keep the wound clean.

The inner layer 12 is elastic in the radial direction. In some embodiments, the inner layer 12 is sufficiently elastic in the radial direction to permit the diameter of the inner layer to stretch to at least 150% or at least 200% of its original diameter in the unstretched state. (As an example, if the original diameter is 3 inches, the inner layer 12 would be sufficiently elastic to stretch to at least 4.5 inches or to at least 6 inches.) The inner layer 12 is preferably also elastic in the axial direction. In some embodiments, the inner layer 12 is sufficiently elastic in the axial direction to permit the length of the inner layer 12 to stretch to at least 110% of its original length in the unstretched state. (As an example, if the original length is 10 inches, the inner layer 12 would be sufficiently elastic to stretch to a length of at least 11 inches.)

The inner layer 12 is designed for direct contact with both intact and compromised skin. In some embodiments, inner layer 12 has nonadherent properties that either prevent the inner layer 12 from adhering to the wound or reduce its adherence to the wound. In alternative embodiments, the material of the inner layer 12 may not be nonadherent, and other approaches for reducing adherence (e.g., use of an ointment) may be relied on. The inner layer preferably seals in moisture to a degree that prevents desiccation of both the ointment layer (when ointment, which is optional, is used) and the surface of the skin to which the wound dressing 10 is applied. The inner layer 12 is also preferably sufficiently permeable and/or absorbent to permit an egress of fluid from weeping wounds, but is not absorbent to such an extent that the ointment would be absorbed into the inner layer 12 (which would cause unwanted desiccation). In some embodiments, material similar to the material used in Mepilex® transfer or Mepitel® dressing is used as the inner layer 12. Note that when one or more of the outer layers are elastic, an adhesive is not necessary to hold the dressing in place. This can be advantageous in situations when a patient has an allergy to adhesives.

In some embodiments, the inner layer 12 may be formed from a plurality of threads or fibers that are woven, knitted, or otherwise formed into the tubular structure, with each of the threads or fibers coated with a substance (e.g., silicone) that prevents or minimizes adherence of the inner layer 12 to the intact or damaged skin beneath that layer. Examples include Silicotex™ Silicone yarn, which is available from Massebeuf Textiles, Pont-de-Labeaume, France.

In alternative embodiments, a substance (e.g., silicone) that reduces or eliminates adherence may be applied (e.g., painted on) to the interior of the inner layer 12 after that layer has been formed. In alternative embodiments, a plurality of longitudinal strips of material may be arranged in a panel formation to form the inner layer 12. In other alternative embodiments, the inner layer 12 may be folded or pleated to improve stretch ability of the inner layer 12.

The first outer layer 15 is disposed adjacent to and radially beyond the inner layer 12 (when the wound dressing 10 is in its non-everted state). The first outer layer 15 may be made of an absorbent material such as fabric gauze that provides absorption of fluids that may leak through the inner layer 12. For example, in some embodiments, a gauze made of Rayon-polyester blend may be used as the first outer layer 15. One suitable supplier of this material is CVS health. In other embodiments, gauze made of 100% cotton (e.g., Kerlix) or a polyester/cotton blend (e.g., Dynarex) may be used. In alternative embodiments, the first outer layer 15 is made of an absorbent gauze-like material instead of true gauze. The first outer layer 15 may also provide padding to protect the patient from impact.

The first outer layer 15 is elastic in the radial direction. In some embodiments, the first outer layer 15 is sufficiently elastic in the radial direction to permit the diameter of the first outer layer 15 to stretch to at least 150% or at least 200% of its original diameter in the unstretched state. The first outer layer 15 is preferably also elastic in the axial direction. In some embodiments, the first outer layer 15 is sufficiently elastic in the axial direction to permit the length of the first outer layer 15 to stretch to at least 110% of its original length in the unstretched state.

A second outer layer 18 is disposed radially beyond the first outer layer 15 (when the wound dressing 10 is in its non-everted state). The second outer layer 18 preferably completely covers the layers disposed within and serves both to protect the interior layers from outside contaminants and to protect the external world from any fluids that may leak outward through the interior layers. The second outer layer 18 preferably also provides a cosmetic function in that it makes the wound dressing appear clean and tidy. Examples of suitable materials that may be used for the second outer layer 18 include Coverflex® and Tubifast™ bandages or the like, or stretchable tubes of material made of Nylon/spandex blends, elastic/polyester blends, elastic tubular gauze, etc. The second outer layer 18 may also provide support for the more medial layers 12, 15.

The second outer layer 18 is elastic in the radial direction. In some embodiments, the second outer layer 18 is sufficiently elastic in the radial direction to permit the diameter of the second outer layer 18 to stretch to at least 150% or at least 200% of its original diameter in the unstretched state. The second outer layer 18 is preferably also elastic in the axial direction. In some embodiments, the second outer layer 18 is sufficiently elastic in the axial direction to permit the length of the second outer layer 18 to stretch to at least 110% of its original length in the unstretched state.

In some embodiments, the second outer layer 18 is immediately adjacent to the first outer layer 15, as depicted in FIG. 1. In alternative embodiments, an additional outer layer (not shown) that provides padding to protect the patient's limb from mechanical trauma is disposed between the first outer layer 15 and the second outer layer 18. Examples of suitable materials for use in this additional layer include foam (such as the material used in the Duro-Med convoluted foam ring), soft rubber, etc.

Any of the layers 12, 15, 18 noted above may be fabricated into its tubular configuration using a variety of techniques including but not limited to circular knitting machines, circular weaving machines, 3D knitting machines, and 3D weaving machines.

Alternatively, any of the layers 12, 15, 18 may be fabricated into its tubular configuration by beginning with a planar piece of material, looping that planar material back on itself so that a first portion of the material will touch a second portion of the material, and connecting the first and second portions of material to form the tube. In these embodiments, any of a variety of alternative approaches may be used to connect the first portion of the material to the second portion of material including, but not limited to stitching, direct bonding, sonic welding, and adhesives. Whatever fastening approach is used, care is preferably taken to ensure that the fastening approach does not interfere with the stretching of the various layers 12, 15, 18. For example, in those embodiments that use stitching, the stitching may be applied in a pattern (e.g., a zigzag pattern) that will not interfere with the stretching of any of the individual layers. In another example, an adhesive may be applied as a series of small dots (e.g., 0.1" diameter) spaced apart at regular intervals (e.g., every 0.5")

Optionally, any two neighboring layers selected from the layers 12, 15, 18 or all three layers 12, 15, 18 may be fabricated together using any of a variety of techniques that will be apparent to persons skilled in the relevant arts including, but not limited to, one or more of the techniques described in U.S. Pat. No. 4,889,063 (Bompard et al.), U.S. Pat. No. 4,506,611 (Parker et al.), and Multiaxis Three Dimensional (3D) Woven Fabric by Kadir Bilisik (which was published as chapter 5 of Advances in Modern Woven Fabrics Technology at pages 79-106).

In some preferred embodiments, the inner layer 12, the first outer layer 15, and the second outer layer 18 are held together via stitching 20. In some embodiments, this stitching is applied as a plurality of zigzag strips that run along the wound dressing 10 in the axial direction, as illustrated in FIGS. 1 and 2. In this case, at least three zigzag strips of stitching 20 are preferably provided. The stitching is preferably implemented using an elastic thread that will not interfere with the stretching of the inner layer 12, the first outer layer 15, or the second outer layer 18, and the stitching is preferably also applied in a pattern that will not interfere with the stretching of those layers. In some embodiments, the stitching does not extend all the way through the inner layer 12 (i.e., inwardly beyond the inner surface of the inner layer 12). These embodiments are advantageous because the inner surface of the inner layer 12 will be smoother.

In alternative embodiments, a different fastening approach may be used to hold the various layers together, including but not limited to direct bonding, staples, clips, sonic welding, adhesives, weaving, knitting, sewing, and stitching. But whatever fastening approach is used, care must be taken to ensure that the fastening approach does not interfere with the stretching of the various layers 12, 15, 18.

In some embodiments, each of the layers 12, 15, 18 and the stitching 20 are sufficiently flexible and stretchable to permit eversion of the wound dressing 10. This is illustrated in FIG. 2 which shows an everted portion 11 of the wound dressing 10.

The elasticity of all the layers 12, 15, 18 described above should be strong enough to hold the wound dressing 10 in place on the patient's body without sliding off due to gravity or movement. On the other hand, the elasticity should be weak enough to prevent interference with the patient's circulation. To this end, it is preferable to make the wound dressing 10 available in a plurality of different sizes for placement on different sized body parts. For example, the wound dressing 10 may be provided in three sizes: one size that is suitable for children's arms; a second size that is suitable for children's legs an adults' arms; and a third size that is suitable for adult legs. Special configurations of the wound dressing 10 may be optimized for use on different body parts including but not limited to fingers or toes (either individually in a glove-like configuration or collectively in a sock-like configuration). In some embodiments, the elasticity of at least one of the layers 12, 15, 18 provides a level of compression that is beneficial for wound healing.

The wound dressing 10 may be applied to the patient's body in a variety of ways, the suitability of which depends on the skin condition being treated. One way to apply the wound dressing 10 is to pull it on to the limb like a sock or glove. Another way to apply the wound dressing 10 is to start off with the wound dressing 10 in an everted configuration in which the inner surface of the inner layer 12 is disposed on the outside of the wound dressing 10, and the second outer layer 18 is disposed on the inside of the wound dressing 10 (similar to the configuration depicted for the everted portion 11 on the left side of FIG. 2). The wound dressing 10 is then positioned at the distal end of the limb onto which it will be applied and pulled in a proximal direction over the limb, so that the wound dressing 10 everts back to the configuration depicted in FIG. 1 as it is pulled over the limb. Optionally, conventional applicators designed for applying tubular bandages may be used to facilitate the application of the wound dressing 10. Examples of suitable applicators that may be used for this purpose include the Ezy-AS™ applicator and the Surgitube® Tubular Bandage Applicator.

The embodiment depicted in FIGS. 1 and 2 includes three layers: the inner layer 12, the first outer layer 15, and the second outer layer 18, and optionally includes an additional layer of ointment 30 that is applied to the inner surface of the inner layer 12. In some alternative embodiments, the first outer layer 15 is omitted. In this case, the wound dressing will include the inner layer 12 and the second outer layer 18, and will optionally include an additional layer of ointment 30 that is applied to the inner surface of the inner layer 12. In other alternative embodiments, the second outer layer 18 is omitted. In this case, the wound dressing will include the inner layer 12 and the first outer layer 15, and will optionally include an additional layer of ointment 30 that is applied to the inner surface of the inner layer 12. In still other alternative embodiments an alternative outer layer (not shown) that combines all of the functionality of the first outer layer 15 and the second outer layer 18 (as described above) may be substituted for both those layers 15, 18 in the FIG. 1 embodiment. In this case, the wound dressing will include the inner layer 12 and the alternative outer layer, and will optionally include an additional layer of ointment 30 that is applied to the inner surface of the inner layer 12. In these two-layer embodiments, any of the individual layers may be fabricated using the approaches described above in connection with FIGS. 1 and 2. And optionally, both layers in the two-layer embodiments may be fabricated together using the techniques described above in connection with FIGS. 1 and 2.

Optionally, a perforation or other region of weakness that runs in an axial direction may be incorporated into one or more of the layers to make it easier to remove the wound dressing from the patient's body. When these regions of weakness are incorporated into more than one of the layers, it is preferable for the regions of weakness to line up with each other.

In alternative embodiments, instead of the structure depicted in FIGS. 1 and 2 that is preformed into a tubular shape, an alternative wound dressing may be provided to the practitioner or patient in a flattened configuration. These embodiments are preferably configured so that the practitioner or patient can reconfigure the wound dressing into its final tubular shape using a zipper, Velcro, or an alternative fastener.

Figure 3:
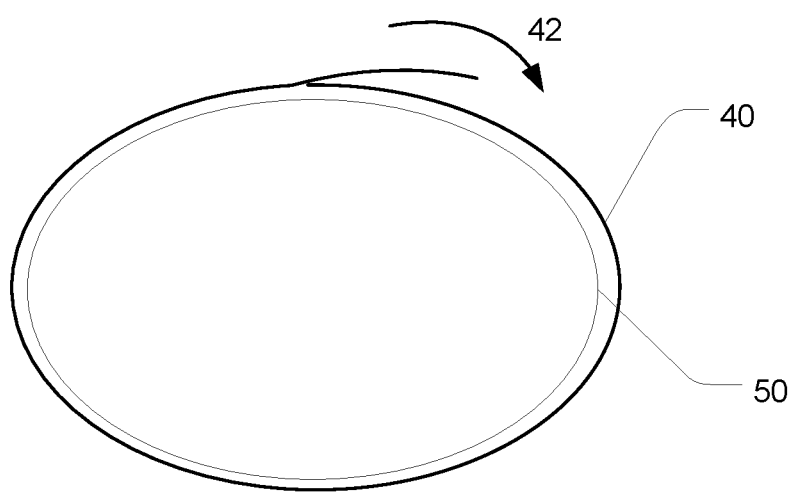
FIG. 3 depicts an alternative embodiment of a multi-layer wound dressing that is placed on as a wrap.

FIG. 3 depicts yet another alternative embodiment in which a multi-layer wound dressing 40 incorporates an adhesive on the innermost surface and is provided to the practitioner or patient in a flattened configuration. This multilayer wound dressing 40 includes an inner layer and at least one outer layer that are similar to the corresponding layers described above in connection with the FIG. 1 embodiment. But instead of starting with pre-formed tubular layers, the practitioner or the patient applies this wound dressing 40 directly against the patient's skin and wraps it around the limb 50 in direction 42 until the entire limb is been covered by the adhesive portion. The practitioner or patient then continues wrapping the wound dressing 40 in the same direction until the remainder of the wound dressing 40 is wrapped over previously-wrapped portions of the wound dressing.

The wound dressings in any of the embodiments described above may be supplied to the practitioner or patient in precut lengths (e.g. 30 inches) with or without ointment pre-applied on the inner surface of the product, and packaged in an air tight sealed, sterile package. Alternatively, the wound dressing in any of the embodiments described above may be supplied on a large roll (e.g., 20 feet), and cut to the desired length by the practitioner or patient.

Note that in addition to their primary intended usage for treating wounds or damaged skin, any of the embodiments described above may also be used on intact skin as well as for the prevention of trauma. And while the wound dressing 10 is described above in the context of treating the skin on human limbs, it may also be used for treating animals.

The embodiments described above can be used to provide some or all of the following advantages over conventional wound dressing techniques: reduced pain, improved ease of use for patients and caregivers, time savings, improved comfort, more seamless contact with large concave and/or convex body surfaces, and more complete wound treatment using a single elasticated tubular structure.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

I claim:

1. A wound dressing comprising:
   a tubular inner layer that permits egress of fluid from weeping wounds, prevents desiccation of skin disposed beneath the inner layer, and prevents desiccation of ointment disposed between the inner layer and the skin;
   a tubular first outer layer disposed adjacent to the inner layer and radially beyond the inner layer, wherein the first outer layer absorbs fluids that leak through the inner layer; and
   a tubular second outer layer disposed radially beyond the first outer layer, wherein the second outer layer protects the first outer layer and the inner layer from outside contaminants and prevents fluids from escaping,
   wherein the first outer layer is affixed to the inner layer and the second outer layer is affixed to the first outer layer,
   wherein each of the inner layer, first outer layer, and second outer layer is elastic in a radial direction; and
   wherein each of the inner layer, first outer layer, and second outer layer is sufficiently elastic in a radial direction to permit a diameter of the wound dressing to stretch to at least 150% of its diameter in an unstretched state.

2. The wound dressing of claim 1, further comprising a layer of ointment that is applied to an inner surface of the inner layer.

3. The wound dressing of claim 1, wherein each of the inner layer, first outer layer, and second outer layer is sufficiently elastic in an axial direction to permit a length of the wound dressing to stretch to at least 110% of its length in the unstretched state.

4. The wound dressing of claim 1, wherein the inner layer has properties that prevent or reduce adherence to wounds.

5. The wound dressing of claim 1, wherein the inner layer is formed from a plurality of threads or fibers, each of which is coated with a substance that prevents or minimizes adherence to the skin.

6. The wound dressing of claim 5, wherein the substance comprises silicone.

7. The wound dressing of claim 1, wherein the first outer layer comprises fabric gauze.

8. The wound dressing of claim 1, wherein the first outer layer is adjacent to the second outer layer.

9. The wound dressing of claim 1, further comprising a layer of a foam material disposed between the first outer layer and the second outer layer.

10. The wound dressing of claim 1, wherein the first outer layer is affixed to the inner layer via stitching and wherein the second outer layer is affixed to the first outer layer via stitching.

11. The wound dressing of claim 10, wherein the stitching is applied as a plurality of zigzag strips that run in an axial direction.

12. The wound dressing of claim 10, further comprising a layer of ointment that is applied to an inner surface of the inner layer,
    wherein each of the inner layer, first outer layer, and second outer layer is sufficiently elastic in an axial direction to permit a length of the wound dressing to stretch to at least 110% of its length in the unstretched state, and
    wherein the inner layer is formed from a plurality of threads or fibers, each of which is coated with a substance that prevents or minimizes adherence.

13. The wound dressing of claim 1, wherein at least one of the inner layer, the first outer layer, and the second outer layer has a region of weakness that runs in an axial direction.

14. A wound dressing comprising:
    a tubular inner layer that permits egress of fluid from weeping wounds, prevents desiccation of skin disposed beneath the inner layer, and prevents desiccation of ointment disposed between the inner layer and the skin; and
    at least one outer layer disposed radially beyond the inner layer, wherein the at least one outer layer absorbs fluid that leaks through the inner layer, protects the inner layer from outside contaminants, and prevents fluids from escaping,
    wherein the at least one outer layer is affixed to the inner layer,
    wherein each of the inner layer and the at least one outer layer is elastic in a radial direction; and
    wherein each of the inner layer and the at least one outer layer is sufficiently elastic in a radial direction to permit a diameter of the wound dressing to stretch to at least 150% of its diameter in an unstretched state.

15. The wound dressing of claim 14, wherein each of the inner layer and the at least one outer layer is sufficiently elastic in an axial direction to permit a length of the wound dressing to stretch to at least 110% of its length in the unstretched state.

16. The wound dressing of claim 14, wherein the at least one outer layer is affixed to the inner layer via stitching.

17. The wound dressing of claim 16, wherein the stitching is applied as a plurality of zigzag strips that run in an axial direction.

18. The wound dressing of claim 16, further comprising a layer of ointment that is applied to an inner surface of the inner layer,
    wherein each of the inner layer and the at least one outer layer is sufficiently elastic in an axial direction to permit a length of the wound dressing to stretch to at least 110% of its length in the unstretched state, and
    wherein the inner layer is formed from a plurality of threads or fibers, each of which is coated with a substance that prevents or minimizes adherence.

19. The wound dressing of claim 14, wherein at least one of the inner layer and the at least one outer layer has a region of weakness that runs in an axial direction.

\* \* \* \* \*